United States Patent [19]

Brown et al.

[11] Patent Number: 4,899,761

[45] Date of Patent: Feb. 13, 1990

[54] APPARATUS AND METHOD FOR MEASURING SPINAL INSTABILITY

[76] Inventors: Mark D. Brown, 9421 SW. 103 St., Miami, Fla. 33176; David C. Holmes, 11262 SW. 169 St., Miami, Fla. 33157

[21] Appl. No.: 175,755

[22] Filed: Mar. 31, 1988

[51] Int. Cl.[4] .............................................. A61B 5/10
[52] U.S. Cl. ..................................... 128/781; 606/191
[58] Field of Search .................... 128/303 R, 341, 345, 128/774–782; 73/862.65

[56] References Cited

U.S. PATENT DOCUMENTS

| | | | |
|---|---|---|---|
| 3,750,652 | 8/1973 | Sherwin | 128/303 R |
| 3,905,356 | 9/1975 | Fletcher et al. | 128/774 |
| 4,132,224 | 1/1979 | Randolph | 128/774 |
| 4,249,417 | 2/1981 | Feldstein et al. | 73/862.65 |
| 4,263,899 | 4/1981 | Burgin | 128/341 |
| 4,432,376 | 2/1984 | Huszar | 128/774 |
| 4,545,374 | 10/1985 | Jacobson | 128/303 R |
| 4,566,465 | 1/1986 | Arhan et al. | 128/341 |

OTHER PUBLICATIONS

1981 Biomechanics Symposium AMD—vol. 43, pp. 291–293, Lubin et al.

Primary Examiner—Max Hindenburg
Attorney, Agent, or Firm—Hedman, Gibson, Costigan & Hoare

[57] ABSTRACT

An apparatus and method for measuring spinal instability provides a vertebrae distractor having a pair of distractor arms driven by a motor which separate adjacent vertebrae of a motion segment unit of the spine at a constant rate of distraction up to a predetermined maximum force and measuring the resistance of the adjacent vertebrae to the force. The changes in the resistance to distraction are detected and recorded. The data thus provided is then compared to predetermined standards. A determination concerning further treatment of the subject patient may be based upon the results obtained.

22 Claims, 3 Drawing Sheets

APPARATUS AND METHOD FOR MEASURING SPINAL INSTABILITY

FIELD OF THE INVENTION

The present invention is directed to an apparatus and method for determining the level of instability of the motion segment unit of the spine and particularly to the lumbar region of the spine. The present invention enables a surgeon to quantitatively determine whether the spine has lost the ability to function under physiological loads in such a way so as to avoid damage and/or irritation to the spinal cord and nerve roots.

BACKGROUND OF THE INVENTION

It is well known that low-back pain is one of the most frequently occurring and expensive disabling ailments, especially for patients in the 30-60 year age bracket. Although low-back pain syndrome is a very common occurrence, its diagnosis to this day is very difficult.

The vertebral column (spine) is a biomechanical structure composed primarily of ligaments, muscles, vertebrae and intervertebral discs. The biomechanical functions of the spine include (1) support of the body (trunk and appendages), which involves the transfer of the weight and the bending moments of the head, trunk and arms to the pelvis and legs, (2) complex physiologic motion between these body parts, and (3) protection of the spinal cord and the nerve roots.

The major regions of the spine are the cervical, thoracic, lumbar and sacral. The vertebrae increase in size and mass from the cervical to the lumbar regions. The increase in size of the vertebrae is directly related to an increased capacity for supporting larger loads. The lumbar region is therefore the major load bearer of the spine. However, this increase in load bearing capacity is paralleled by a decrease in flexibility. Because the lumbar region bears heavier loads than other regions of the spine, the lumbar trunk (low back structure) is more susceptible to strain and hence low-back pain.

The spine is comprised of different levels known as motion segment units. The lumbar spine is comprised of five motion segment units. The motion segment unit is the smallest component of the spine that exhibits kinematic behavior similar to that of the whole spine. The motion segment unit is capable of flexion, extension, lateral bending and translation. The components of each motion segment unit include two adjacent vertebrae and their apophyseal joints, the intervertebral disc and the connecting ligamentous tissue.

Many causes of low-back pain are attributed to the instability of the motion segment unit. Segmental instability is defined as "the loss of ability of the spine under physiologic loads to maintain relationships between vertebrae in such a way that there is neither damage nor subsequent irritation to the spinal cord or nerve roots, and, in addition, there is no development of incapacitating deformity or pain due to structural changes". In other words, instability is an abnormal response to applied loads characterized by motion in the motion segment unit beyond normal constraints. Excess motion can be abnormal in quality (i.e., abnormal coupling patterns) or in quantity (abnormal increased motion) or both. Excess motion results in damage to the nerve roots, the spinal cord, and other spinal structures.

The underlying causes of the structural changes in the motion segment unit leading to instability are trauma, degeneration, aging, disease (tumor, infection, etc.), surgery, or a combination thereof. It is known that a mechanically unstable motion segment unit can originate due to degeneration of the nucleus pulposus. A degenerate nucleus causes disc space narrowing, loss of viscoelastic properties and the subsequent transfer of compressive loads to the annulus fibrosus. The altered anatomic dimensions and subsequent abnormal response to loading can cause loss of pre-tension in the ligamenum flavum, and longitudinal ligaments, degeneration of the facet capsules (and possible subluxation) with a consequence of secondary degenerative osteoarthritis of the joints.

Spinal disorders requiring neural decompressive surgery can leave motion segment units unstable due to the removal of supporting structures of the joint. A severely unstable motion segment unit is most likely to be fused to insure post-surgical stability. The need to fuse the vertebrae of a motion segment unit is dependent on the pre-operative symptoms and clinical (radiographic) findings and on the outcome of the surgical procedure.

One effort at mechanically determining spinal instability is disclosed in "A Technique for Mechanical Assessment of the Interverebral Joint", Mark Lubin et al., *Biomech. Sym.* ADM vol. 43 (1981). A Cloward lamina spreader is fitted with a strain gauge and loading and unloading of force is conducted manually. The device disclosed in the aforementioned publication is disadvantageous because there is no recognition of the need to control the rate of displacement nor a means for doing so which enables precise measurements of relative stiffness of the motion segment unit. The motion segment unit is a viscoelastic structure and therefore its resistance to deformation is dependent on the loading rate. To date, there are no objective criteria for determining the degree of instability of the motion segment unit and whether spinal fusion surgery is necessary to relieve low-back pain in the patient.

It is therefore an object of the invention to provide an apparatus and method for measuring instability of a motion segment unit of the spine.

It is another object of the present invention to provide an apparatus and method for measuring instability of a motion segment unit of the spine wherein the loading and unloading of force can be conducted at a constant rate in order to enable precise measurements, which cannot be accomplished by prior art systems.

It is another object of the invention to provide an apparatus and method which serves as a diagnostic aid for determining the desirability of performing spinal fusion surgery at the time of the decompressive surgical procedure.

It is a further object of the invention to provide a method of measuring spinal instability.

SUMMARY OF THE INVENTION

In accordance with the above-mentioned objectives, the present invention provides an apparatus and method for measuring instability of the motion segment unit of the spine by providing a vertebrae distractor including means for applying a constant rate of increasing force against adjacent vertebrae of a motion segment unit to thereby distract or separate the vertebrae and means for detecting and recording the changes in the resistance to distraction. For example, the changes in the resistance to distraction may be recorded as relatively small changes in voltage, which is then translated into a force per unit length of distraction.

In other words, the present invention provides an apparatus which comprises:

distraction means for applying a force to and separating adjacent vertebrae of the motion segment unit at a constant rate of distraction, and detection means connected to said distraction means for measuring the resistance of the adjacent vertebrae to said distraction at a plurality of force-exerting positions, said detection means generating an output signal corresponding to said resistance.

In addition, the present invention relates to a method for measuring the instability of a motion segment unit of a spine which comprises:

placing distraction means between adjacent vertebrae;

moving the distraction means at a constant rate from a relaxed position exerting no force on the adjacent vertebrae to a plurality of force exerting positions;

detecting the resistance of the separated vertebrae to the force which is exerted on the adjacent vertebrae in said force exerting positions and generating an output signal corresponding to the resistance;

terminating movement of the distractor means at a force exerting position corresponding to a predetermined maximum resistance to said force by the adjacent vertebrae; and converting the output signal into interpretable data (e.g., force per unit length of distraction) which can be compared with previously determined standards, e.g. data obtained from known motion segment units.

More specifically, the distraction means of the present invention comprises a vertebrae distractor which includes a pair of adjacent distractor arms, a supporting frame, guiding means such as a power screw having right and left hand threads to which the distractor arms are threaded upon, and driving means, for example, a power source capable of providing variable speeds and torque such as a stepper motor. The arms are attached to the frame via a combination of a screw and swivel hinge. The frame is adapted to limit the motion of the arms in one plane, whereby the arms move away from each other to thereby distract or move apart the vertebrae, and then toward each other to relax the vertebrae.

Limiting means is provided in the frame to limit the distance of displacement between the two vertebrae by operation of the distraction means so as to prevent fracture or dislocation of the vertebrae. One end of the arms rotate freely about upper fixed pivots. Below and within the top of each arm is a second pivot. The power screw is threaded through both of the second pivots. The portion of the screw closest to the stepper motor has a right-hand or left hand thread and the remaining portion is threaded in the opposite direction. This interface between the screw and the arm enables rotational displacement of the arms. Thus, a clockwise or counterclockwise rotation of the screw causes the arms to simultaneously open (i.e., move away from one another) or close (i.e., come together) respectively in one plane. The driven pivots linking the arms and the power screw insure that any load applied to the bottom of the arms in contact with the vertebrae always results in the screw being loaded compressively. The rotational motion of the screw is therefore not impeded. Small gripping means (e.g., teeth) are provided at the bottom of the arms to secure the apparatus to the adjacent vertebrae during operation.

The apparatus also includes means for measuring the resistance of the vertebrae to the applied force and for measuring the degree of displacement. In one embodiment of the invention, the resistance measuring means is a strain gauge which measures changes in resistance as a relatively small change in voltage. The apparatus also comprises a signal conditioning circuit which magnifies or amplifies the small changes in voltage so that the change in voltage can be converted into an interpretable signal. Also forming part of the present invention is translation means for comparing the resistance and displacement of the adjacent vertebrae to measurements taken from known motion segment units so that a relative comparison can be made. This comparison enables one to determine the proper treatment for the patient. For example, if the subject motion segment unit significantly inhibits more motion than desired, spinal fusion surgery may be in order.

In operation, the arms of the apparatus are placed between the spinous process of adjacent vertebrae in a manner such that the teeth at the bottom end of the respective arms engage the base of the spinous processes at their function with the lamina. The stepper motor is then activated causing the power screw to rotate in a direction which forces the arms to move in a single plane away from each other and in the transverse direction of the spinal column to thereby move the adjacent vertebrae away from each other (i.e., to displace the vertebrae). The stepper motor is set so as to apply a force against the adjacent vertebrae so that a constant rate of distraction is attained until a predetermined maximum force is attained.

In another embodiment of the present invention, the arms of the apparatus also are reversibly movable in the opposite direction so that the distracted vertebrae may move toward their original position at a constant rate. This enables further measurements to be made of the relative stiffness of the motion segment unit.

The onset of resistance offered by the adjacent vertebrae is measured by at least one strain gauge affixed to either or both of the arms. The strain gauge interprets the force applied as a small change in voltage (i.e., a millivolt change) and conveys a signal corresponding to the change in voltage to a signal conditioning circuit which amplifies the voltage so that it can be read by an analog to digital converter which translates the voltage change into units of force (i.e., Newtons).

The data obtained from a series of displacements of one motion segment unit is based on the application of increased force to obtain a plurality of force per unit length of displacement measurements (e.g., Newtons per millimeter) and is compared to results obtained from motion segment units in unfixed cardaveric spines and in some cases to the surgeon's subjective testing using, for example, a Kocher clamp known to those skilled in the art. The degree of stiffness from the Kocher clamp test is assigned a value from 1 (extreme compliance) to 10 (extreme stiffness) by the surgeon based upon his/her tactile sense and experience.

BRIEF DESCRIPTION OF THE DRAWINGS

The following drawings in which like reference numerals indicate like parts are illustrative of embodiments of the present invention and are not meant to limit the invention as defined by the scope of the claims forming part of the application.

DETAILED DESCRIPTION OF THE DRAWINGS

Figure 1:
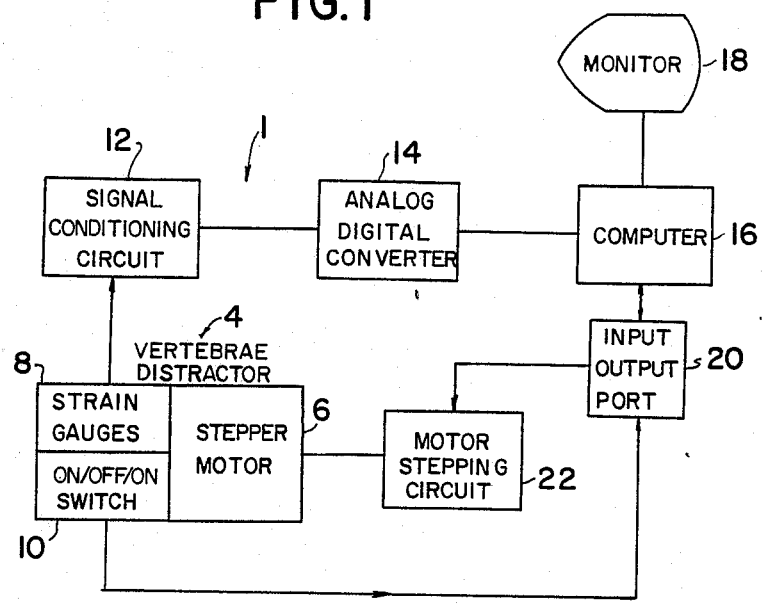
FIG. 1 is a schematic view of the present invention for evaluating instability of the motion segment unit of the lumbar spine.

Referring to the drawings and specifically to FIG. 1, the apparatus 1 of the present invention includes a vertebrae distractor 4 which is comprised of a stepper motor 6 capable of applying a force to the vertebrae distractor 4. The stepper motor 6 (e.g. model 45H-24A56S sold by Airpax, Inc.) is variable in both speed and torque. The torque and rotational speed produced by the motor is dependent upon the power available to the motor. Thus, the rotational speed of the motor is variable, depending on the rate at which a computer 16 sends voltage impulses via an imput/output port 20 through a motor stepping circuit 22 to the stepper motor 6. Each voltage pulse can be set to a constant rate of motor revolution (e.g., 1.8 degrees) so that, for instance, 200 pulses are required for each revolution of the stepper motor 6.

The input/output port 20 of the computer 16 sends a signal in the form of a voltage pulse (e.g., 12 volts) to the motor stepping circuit 22 to control the rate at which the stepper motor 6 rotates. Each pulse is sufficient to cause the stepper motor 6 to rotate at a constant rate (e.g. 1.8 degrees). A desired pulse rate has been found to be between about 30 to about 60 pulses (e.g. 40 pulses per second). If the rate of rotation is too slow, the motion segment unit will tend to "creep" or undergo additional distraction which leads to a false reading of stiffness. It is critical that the rate of the distraction be constant in order to accurately determine the degree of stiffness, which is measured by dividing the resulting force by the distance of distraction.

The strain gauges 8 operate as a load transducer and detect the resistance of the adjacent vertebrae to the force being applied by the vertebrae distractor 4, and translate the same into a voltage (in millivolts). Accordingly, the voltage produced by strain gauges 8 is a function of the resistance to the force applied, and is translated into a voltage, which is typically in the range from 0 (no load) to about 12 millivolts (maximum load). A maximum voltage of about 12 millivolts is equivalent to about 200 newtons of stress, since the voltage varies directly with the stress.

The strain gauge 8 transmits a signal corresponding to the change in voltage to a signal conditioning circuit 12 which has a two-fold function. First, the signal conditioning circuit 12 filters out extraneous voltage interference such as minute voltage signals emanating from fluorescent lights, etc. and, second, it amplifies the voltage signal from the strain gauges 8 from mV to V units so that the change in voltage may be read by an analog to digital converter 14. The signal conditioning circuit 12 translates the millivolt signal from the stress gauge 8 into a voltage readout of from 0–10 volts, or other suitable range as desired.

The analog to digital converter 14 converts the amplified signal from the signal conditioning circuit 12 into force units, (e.g., newtons) which can be read by computer 16. For example, the converter 14 converts the voltage from the signal conditioning voltage (e.g., 0–10 volts) to a digital readout of, for example, 0 to 255 units. The computer 16 is equipped with stored data which can interpret and convert the maximum value (i.e., 255 units) as the maximum load (e.g., 200 newton load) applied to the vertebrae. The results may be viewed on a monitor 18 and compared to previously acquired data such as data acquired from motion segment units of normal subjects having similar physiologic backgrounds.

The apparatus is provided with safety mechanisms in order to prevent the vertebrae distractor 4 from exerting a load upon the adjacent vertebrae which would be large enough to cause a fracture of the spinous processes. The safety mechanisms comprise (1) a program in computer 16 such that when the distraction force exceeds a preset value the impulses to the motor are no longer transmitted, thus causing it to stop, and (2) the available power to the motor as set by the circuit design 12 limits the distraction force to 200 newtons.

Figure 2:
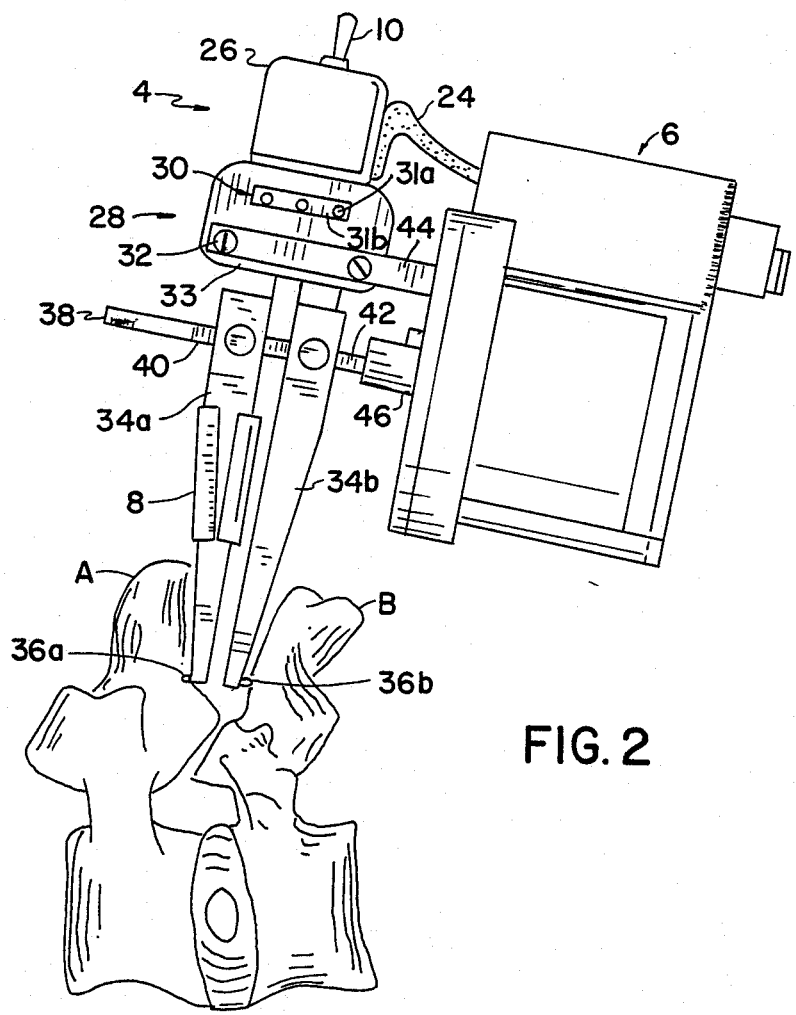
FIG. 2 is a perspective view of the vertebrae distractor of the present invention inserted between adjacent vertabrae of a motion segment unit.
Figure 3:
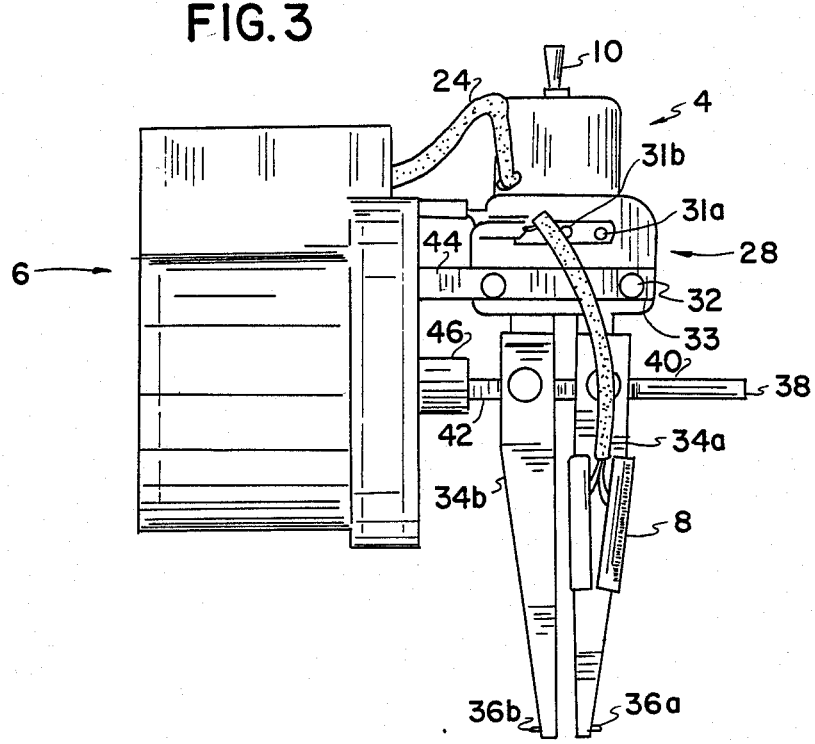
FIG. 3 is a side elevational view of the apparatus shown in FIG. 2.
Figure 4:
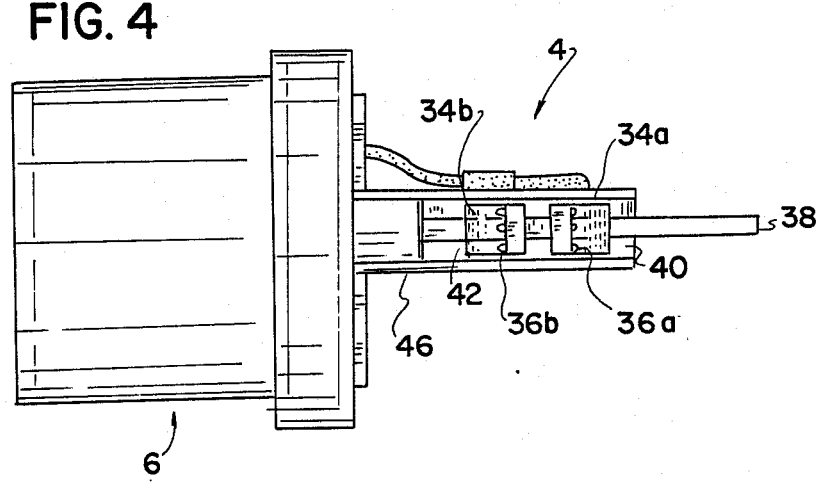
FIG. 4 is a bottom view of the apparatus shown in FIG. 2.

As shown in FIG. 2, the apparatus of the present invention is placed into operation by placing the vertebrae distractor 4 into position between adjacent vertebrae as described hereinafter and then activating the stepper motor 6 by moving switch 10 to the "on" position. The system is deactivated by moving the switch 10 to the "off" position and removing the vertebrae distractor 4 from its position between the adjacent vertebrae. In accordance with the present invention, the system may be used in the operating room to enable the surgeon to quantitatively determine whether fusion of a motion segment unit is necessary to insure stability at the level of the spine in question.

The vertebrae distractor 4 of the present invention includes a stepper motor 6 as previously described and a pair of distractor arms 34a and 34b insertable between adjacent vertebrae A and B (see FIG. 2). The stepper motor 6 is affixed to a frame 28 via support means 33 which is comprised of a bar 44 and screws 32. The frame 28 also supports the distractor arms 34a and 34b and a switch housing 26, which contains switch 10. Switch 10 is used to activate the distractor arms 34a and 34b via a relay 24 from the stepper motor 6.

Each of the distractor arms 34a and 34b are pivotally attached to the frame 28 by fixed pivots 30 made up of screws 31a and 31b. The screws 31a and 31b provide support for the distractor arms 34a and 34b and act as limiting means to physically limit the maximum distraction between the distraction arms 34a and 34b, thus avoiding undesirable loads on the vertebrae.

Figure 5:
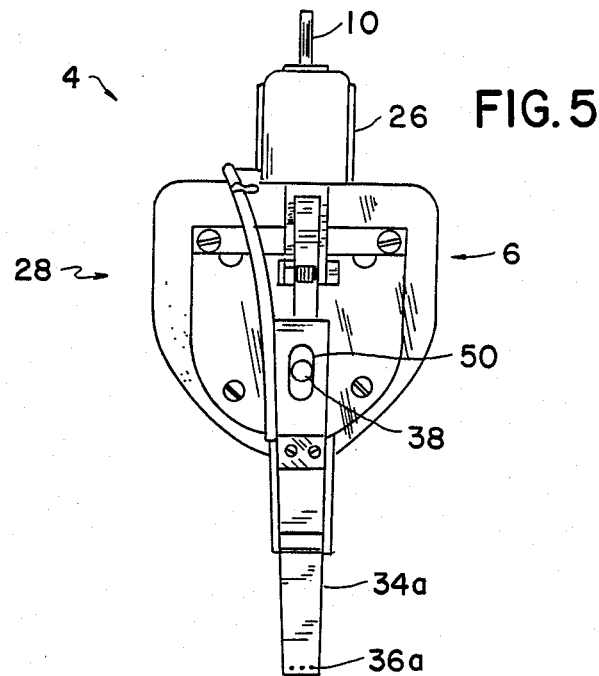
FIG. 5 is a front view of the apparatus shown in FIG. 2.

The distractor arms 34a and 34b are movably connected to the stepper motor 6 by a non-conducting pin 46 having therein a power screw 38. The power screw 38 is equipped with left hand threads 40 and right hand threads 42. The power screw 38 rotates within an opening 50 (see FIG. 5) within the distractor arms 34a and 34b. Rotation of the power screw 38 results in a translational movement of the distractor arms 34a and 34b away from and toward each other in a single plane as described hereinafter. Thus, one revolution of the stepper motor 6, for example, at 1.8 degrees of rotation per voltage pulse, can cause the distractor arms 34a and 34b to move apart a distance of approximately 0.5 cm. Although the loading rate can be varied depending upon any number of factors including differences from subject to subject and possibly differences in the data sought, a motor stepping rate of 40 steps/second (0.2 rev/sec) or a 0.102 cm/sec distraction rate has been found to provide the most significant data concerning a motion segment unit.

At least one of the distractor arms 34a and 34b is equipped with a pair of strain gauges 8 which measure the resistance to distraction generated when the distractor arms 34a and 34b distract the adjacent vertebrae A and B and generate a voltage signal (in mV) in response. In the instant example, the resistance measured by the strain gauges 8 is caused by a controlled bending of the distractor arms 34a and 34b, thereby producing different voltage outputs which correspond to changes in the resistance to distraction. The voltage signal is relayed to the signal conditioning circuit 12 via shielded cable 48 (not shown) for eventual analysis by the computer 16 as previously described.

Each of the lower ends of the distractor arms 34a and 34b have teeth 36a and 36b, respectively which are used to engage the adjacent vertebrae A and B to insure against slippage. In operation, the distractor arms 34a and 34b are firmly seated between adjacent vertebrae A and B such that teeth 36a are placed in contact with vertebrae A and teeth 36b likewise engage vertebrae B of the motion segment unit. The vertebrae distractor 4 is then activated via the switch 10 causing power screw 38 to rotate such that the distractor arm 34b is caused to move along right hand threads 42 and the distractor arm 34a moves in the opposite direction in a single plane along left hand threads 40. The computer 16 (see FIG. 1) controls the rate of distraction via the input/output port 20 and the motor stepping circuit 22 by outputting discreet voltage impulses which rotate the stepper motor 6 a preset amount of rotation (e.g. 1.8 degrees) per voltage impulse. Accordingly, the distractor arms 34a and 34b move at a constant rate and thereby apply a force against the adjacent vertebrae A and B until a maximum load (i.e., no more than about 200 newtons of force) is achieved.

In a preferred embodiment of the instant invention, the switch 10 is an on/off/on switch, which in one "on" position allows the distractor arms 34a and 34b to move away from each other (thereby exerting a force against the adjacent vertebrae) and allows the distractor arms 34a and 34b to move toward each other after a predetermined maximum force is applied. Thus after the maximum force is applied, the switch 10 is moved to reverse the rotation of the stepper motor 6 to move the distractor arms 34a and 34b toward each other, thereby relieving pressure against the adjacent vertebrae A and B, which then return to their relaxed or non-distracted state.

In another embodiment of the present invention, measurements are also taken during the reverse motion of the distractor arms 34a and 34b (i.e., while relieving the force) at a plurality of positions in order to obtain additional interpretable data.

Figure 6:
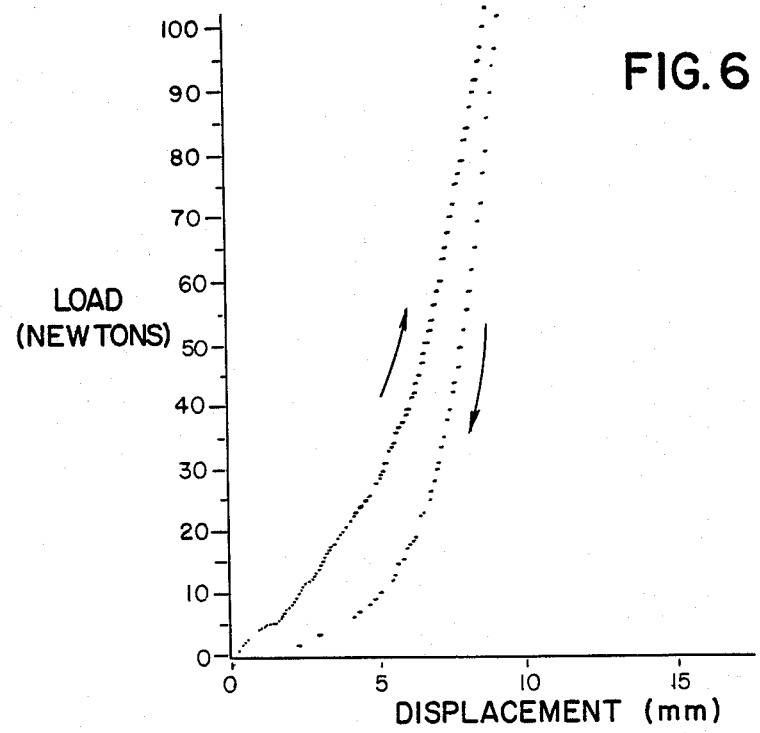
FIG. 6 is a graph showing the results of a distraction test using the apparatus and system of the present invention.

As shown in FIG. 6, the outcome of a single distraction test is a plot of measured load (force) against the adjacent vertebrae versus the degree of displacement (i.e. distance). The relative stiffness of the motion segment unit is determined from the slope of the plot and is proportional to the stability of the motion segment unit. The slope is measured at various levels of load and displacement and the slope values are compared to slopes for previously determined motion segment units.

The plot depicted in FIG. 6 shows the data obtained during both the force-exerting movement and force-relieving movement of the distractor arms 34a and 34b.

In addition to the examples set forth above, many variations of the present invention will suggest themselves to those skilled in the art in light of the above detailed description. For instance, it is contemplated that other devices may be used to detect the resistance to distraction which may not generate an output voltage as such, but would instead provide different types of interpretable signals. All such obvious variations are within the full intended scope of the appended claims.

What is claimed is:

1. An apparatus for measuring instability of a motion segment unit of a spine comprising:
   distraction means for applying a force to and thereby separate adjacent vertebrae of the motion segment unit at a constant rate;
   detection means connected to said distraction means for measuring the resistance of the adjacent vertebrae to said distraction, at a plurality of force-exerting positions, said detection means generating an output signal corresponding to said resistance;
   translation means adapted to receive said output signal from said detection means and for translating said output signal into interpretable data corresponding to the relative stiffness of the motion segment unit; and
   safety means operatively engaged when the resistance of the adjacent vertebrae to the distraction generated by the distraction means reaches a predetermined level.

2. The apparatus of claim 1 wherein the distractor means is adapted to apply a force to a motion segment unit of the lumbar region of the spine.

3. The apparatus of claim 1, wherein said output signal comprises an output voltage and said translation means comprises:
   amplification means for receiving said output voltage from said detection means and amplifying said output voltage into a detectable signal, and
   signal detection means for receiving said detectable signal and translating said detectable signal into said interpretable data.

4. The apparatus of claim 3, wherein said signal detection means comprises converting means and computation means, said converting means receiving said detectable signal from said amplification means and converting said detectable signal into force units which are readable by said computation means.

5. The apparatus of claim 4 wherein said computation means is operable to compare said force units with stored data.

6. The apparatus of claim 1, wherein the safety means is adapted to disengage said distraction means when the resistance of the adjacent vertebrae to said distraction reaches a predetermined level.

7. The apparatus of claim 1, wherein said distraction means comprises:
   separator means including a pair of vertebrae distractor arms, said arms being movable from a relaxed position exerting no force on the vertebrae to a plurality of force exerting positions thereby moving the adjacent vertebrae from said relaxed position to said force exerting positions.

8. The apparatus of claim 7, wherein the safety means is adapted to prevent further movement of the pair of vertebrae distractor arms when the resistance of the adjacent vertebrae to said distraction reaches a predetermined level.

9. The apparatus of claim 7, wherein said distraction means further comprises driving means operatively connected to the separator means for reversibly moving said distractor arms at a constant rate of distraction from said relaxed position to said force exerting positions.

10. The apparatus of claim 9, wherein said safety means disengages the driving means when the resistance of the adjacent vertebrae to said distraction reaches a predetermined level.

11. The apparatus of claim 9, wherein said distraction means further comprises guiding means for guiding said distractor arms in a single plane in opposite directions when the adjacent vertebrae are moved to said force exerting positions.

12. The apparatus of claim 11, further comprising a frame, wherein one end of said distractor arms are guided by said guiding means within a single plane in said frame towards and away from each other, said distractor arms having remote ends for contacting the adjacent vertebrae.

13. The apparatus of claim 12, wherein said safety means comprises means for limiting the movement of said distractor arms in said frame, said limiting means engaging said distractor arms at a position of maximum allowable distraction, thereby preventing said distractor arms from exerting greater force.

14. The apparatus of claim 9, wherein said computation means is connected to said driving means, said computation means causing said driving means to provide a force against the adjacent vertebrae, thereby allowing said distractor arms to separate the adjacent vertebrae at a constant rate.

15. The apparatus of claim 11, wherein said driving means includes means for reversing the movement of said distractor arms at a constant rate to a plurality of force relaxing positions to thereby enable said adjacent vertebrae to retract toward their original position, said detection means being operable to detect the resistance of said adjacent vertebrae to said decreasing force and generating an output signal corresponding to said resistance.

16. The apparatus of claim 15, further comprising threaded means having oppositely directed threading, said distractor arms being threaded through said threaded means, wherein said driving means is connected to said threaded means to rotate in a force 17. The apparatus of claim 16, wherein said driving means comprises a stepper motor.

18. The apparatus of claim 7, wherein said distractor arms include engaging means at said remote ends for engaging the adjacent vertebrae.

19. The apparatus of claim 7, wherein said detection means comprises at least one strain gauge connected to at least one of said distractor arms, said strain gauge interpreting the resistance of the adjacent vertebrae to said force exerted by said distractor arms as a change in voltage and generating a corresponding output voltage.

20. A method of measuring instability of a motion segment unit of a spine, comprising:
    (a) placing distraction means between adjacent vertebrae;
    (b) moving said distraction means from a relaxed position exerting no force on the adjacent vertebrae to a plurality of force exerting positions in a manner in which the adjacent vertebrae are distracted at a constant rate;
    (c) detecting the resistance of the adjacent vertebrae to the force which is exerted and generating an output signal corresponding to the resistance of the adjacent vertebrae to said force;
    (d) terminating movement of the distractor means at a force exerting position when a predetermined maximum resistance by the adjacent vertebrae to said force is detected; and
    (e) converting said output signal into interpretable data which can be compared against predetermined standards.

21. The method of claim 19, further comprising:
    moving said distraction means from a maximum force exerting position to a plurality of force relieving positions such that the adjacent vertebrae move toward their original position at a constant rate;
    detecting the resistance of the adjacent vertebrae to said force relieving positions and generating a corresponding output signal; and
    converting said output signal into interpretable data corresponding to the relative stiffness of the motion segment unit.

22. The method of claim 21 further comprising comparing said data to a predetermined standard.

* * * * *

UNITED STATES PATENT AND TRADEMARK OFFICE
CERTIFICATE OF CORRECTION

PATENT NO. : 4,899,761
DATED : February 13, 1990
INVENTOR(S) : Mark D. Brown Et Al.

It is certified that error appears in the above-identified patent and that said Letters Patent is hereby corrected as shown below:

Claim 16, column 10, line 2, insert the following:

-- exerting direction and in a force relaxing direction, said distractor arms moving away from each other when said threaded means is rotated in said force exerting direction and toward each other when said threaded means is rotated in the said force relaxing direction. --

Claim 21, column 10, line 34, "19" should read -- 20 --.

Signed and Sealed this

Tenth Day of March, 1992

Attest:

HARRY F. MANBECK, JR.

*Attesting Officer*  *Commissioner of Patents and Trademarks*